(12) United States Patent
Smith

(10) Patent No.: US 8,150,625 B2
(45) Date of Patent: Apr. 3, 2012

(54) SYSTEM AND METHOD FOR CLASSIFYING A BODY TISSUE SAMPLE

(75) Inventor: Yoav Smith, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 1189 days.

(21) Appl. No.: 10/592,309

(22) PCT Filed: Mar. 13, 2005

(86) PCT No.: PCT/IL2005/000288
§ 371 (c)(1),
(2), (4) Date: Jul. 31, 2007

(87) PCT Pub. No.: WO2005/088513
PCT Pub. Date: Sep. 22, 2005

(65) Prior Publication Data
US 2007/0281301 A1 Dec. 6, 2007

Related U.S. Application Data

(60) Provisional application No. 60/551,791, filed on Mar. 11, 2004.

(51) Int. Cl.
*G06F 7/00* (2006.01)

(52) U.S. Cl. ............ 702/19; 702/20; 703/11; 707/700; 435/6.1

(58) Field of Classification Search .................. None
See application file for complete search history.

(56) References Cited

U.S. PATENT DOCUMENTS
6,631,204 B1 10/2003 Smith

OTHER PUBLICATIONS

Bicciato, S., et al., "Disjoint PCA models for marker indentification and classification of cancer types using gene expression data", *Minerva Biotec*, vol. 14, pp. 281-290, (2002).
Musumarra, G., et al., "A Bioinformatic Approach to the Identification of Candidate Genes for the Development of New Cancer Diagnostics", *Biol. Chem.*, vol. 384, pp. 321-327, (2003).
Golub, T.R., et al., "Molecular Classification of Cancer: Class Discovery and Class Prediction by Gene Expression Monitoring", *Science*, vol. 286, pp. 531-537, (1999).
Dudoit, S., et al., "Comparison of Discrimination Methods for the Classification of Tumors Using Gene Expression Data", *Journal of the American Statistical Association*, vol. 97, No. 457, pp. 77-87, (2002).
Liu, H., et al., "On Issue of Instance Selection", *Data Mining and Knowledge Discovery*, vol. 6, pp. 115-130, 2002).
Ramaswamy, S., et al., "Multiclass cancer diagnosis using tumor gene expression signature", *PNAS*, vol. 98, pp. 15149-15154, (2001).
Yeoh, E-J., et al., "Classification, sub-type discovery, and prediction of outcome in pediatric acute lymphoblastic leukemia by gene expression profiling", *Cancer Cell*, vol. 1, pp. 133-143, (2002).

*Primary Examiner* — Mary Zeman
(74) *Attorney, Agent, or Firm* — Susanne M. Hopkins; Ari G. Zytcer

(57) ABSTRACT

A method for classifying a test tissue sample into a class from among K classes, where the test tissue sample has an associated gene expression vector is provided. For each class k from among the K classes, a gene expression matrix is provided based upon a gene expression level in one or more tissue samples known to be in the class k. One or more eigenvectors of the covariance matrix $C_x$ of the centralized gene expression matrix are calculated. A metric $\mu_k$ that is indicative of the extent of dissimilarity between the gene expression vector and the gene expression matrix is calculated using an algebraic expression involving one or more of the eigenvectors of the matrix $C_x$. The test tissue sample is then classified into a class k for which the metric $\mu_k$ is minimum among the k classes.

15 Claims, 2 Drawing Sheets

SYSTEM AND METHOD FOR CLASSIFYING A BODY TISSUE SAMPLE

CROSS-REFERENCE

This is a National Phase Application filed under 35 U.S.C. 371 of International Application No. PCT/IL2005/000288, filed on Mar. 13, 2005, claiming the benefit under 35 USC 119(e) of U.S. Provisional Patent Application No. 60/551,791, filed on Mar. 11, 2004, the entire content of which is hereby incorporated by reference in its entirety.

FIELD OF THE INVENTION

This invention relates to diagnostic systems and methods, and more particularly to such systems and methods for the diagnosis of genetic diseases.

BACKGROUND OF THE INVENTION

Microarrays of nucleic acids are used to detect nucleic acid molecules in a sample. The microarray consists of different nucleic acid molecules (referred to as the "probe nucleic acids") that are immobilized on a solid support (sometimes referred to as a "chip"). Each nucleic acid probe is immobilized on the chip at a known location. A sample, possibly containing nucleic acid sequences (referred to as "target nucleic acids"), is then presented to the probe nucleic acid molecules immobilized on the chip. Complementary binding of a target nucleic acid in the sample to a probe nucleic acid molecule on the chip generates a detectable signal, for example a fluorescent signal. The intensity of the detectable signal is proportional, or at least indicative, of the abundance of the target nucleic acid in the sample. A large number (typically over 1,000) of probe nucleotide sequences may be immobilized on the chip, so that an equally large number of target sequences in the sample, may be detected simultaneously using a single chip.

Microarray techniques have been used to compare gene expression levels in different tissues, or for comparing expression levels in healthy and diseased tissue of the same type. The level of gene expression in a given tissue provides a signature of the tissue. Similarly, the level of gene expression in a diseased tissue provides a signature of the disease.

In principle, the signature of gene expression in a tissue can be used to diagnose a disease in the tissue. For example, it is known that the various forms of leukemia are distinguishable by their characteristic pattern of gene expression. For this, the level of gene expression in the tissue is determined in the individual and compared with that previously obtained from an individual having the disease and from a healthy individual. In practice, however, the diagnosis is complicated by variability in the gene expression in the tissue type in different healthy individuals and in different individuals having the disease as well as the similarity of the gene expression level in the same tissue in different, but related diseases, such as various forms of leukemia.

SUMMARY OF THE INVENTION

The present invention provides a system and method for classifying a tissue sample into two or more classes where each class has a characteristic pattern of gene expression of a predetermined set of genes. For example, a tissue sample of a particular tissue type may be classified into one of two classes, one class being that the tissue sample is healthy and the other class being that the tissue is diseased. In this case, the pattern of gene expression in this tissue type in the healthy state is different from the pattern of gene expression in this tissue type in a diseased state. As another example, a tissue sample may be classified into K classes, where each class is that the tissue has a specific disease (or lack thereof), where each disease has a characteristic pattern of gene expression. As yet another example, a tissue sample may be classified into two or more classes where each class is that the individual from whom the tissue sample was obtained responds in a class-specific manner to a particular treatment, such as a particular drug treatment or radiotherapy. As yet further examples, a tissue sample may be classified into two or more classes where one or more of the classes is that the individual from whom the tissue sample was taken is in a state of remission for a particular disease, or is in a state of relapse of a particular disease.

In accordance with the invention, for each of a number of K classes into which a tissue sample is to be classified, a genetic database is provided. For each class k, where k=1 to K, provision of the database involves providing an expression level of each gene in a predetermined set of N genes in $M_k$ tissue samples known to belong to that class. The expression level of the N genes in the tissue sample is also provided, and a metric, $\mu_k$, described below, is calculated for each of the K classes, where $\mu_k$ is a measure of the dissimilarity of the pattern of gene expression in the tissue sample and the database of that class. The tissue sample is then classified in the class $\tilde{k}$, where $\tilde{k}$ is the value of k for which $\mu_k$ is minimal.

A level of gene expression may be determined a the level of transcription, the level or translation, or the level of protein processing. Thus, a level of gene expression may be determined by determining the abundance of mRNA transcripts to the gene in the tissue sample, the abundance of a protein encoded by the gene in the tissue sample, or the abundance of a processed protein (e.g. a particular phosphorylated protein) in the tissue sample. A level of gene expression may be determined by any method for producing such information, such as microarray analysis. The publications of Ramaswamy et al and Enj-Juh et al. disclose methods for obtaining gene expression levels using microarray analyses. Other methods for obtaining a gene expression level include Southern blots and Western blots.

For example, if the tissue type is blood and the class is that the tissue sample has a particular form of leukemia, then provision of the database involves providing an expression level of each of N predetermined genes in $M_k$ blood samples obtained from individuals having that particular type of leukemia. The expression $x_{ij}^k$ is used herein to denote the expression level of the gene j (in the set of N genes) in the tissue sample i, known to belong to the class k, where i=1, . . . $M_k$, j=1, . . . N, and k=1, . . . K. Thus, for each class k, k=1 to K, the database of the disease k may be represented as an $NXM_k$ matrix $X^k$, where $$X^k = \begin{vmatrix} x_{11}^k & x_{21}^k & x_{31}^k & \cdots & x_{M_k 1}^k \\ x_{12}^k & x_{22}^k & x_{32}^k & \cdots & x_{M_k 2}^k \\ \cdots & \cdots & \cdots & \cdots & \cdots \\ \cdots & \cdots & \cdots & \cdots & \cdots \\ x_{1N}^k & x_{2N}^k & x_{3N}^k & \cdots & x_{M_k N}^k \end{vmatrix}$$

The vector $$X_i^k = \begin{pmatrix} x_{i1}^k \\ x_{i2}^k \\ \vdots \\ x_{iN}^k \end{pmatrix}$$

is the ith column vector of $X^k$ and is the vector of the gene expression levels of the individual i in the class k.

The mean vector of the gene expression levels of the $M_k$ individuals in the class k is $$\overline{M}_k = 1/M_k * \sum_{i=1}^{M} X_i^k.$$

The matrix obtained from the matrix $X^k$ by subtracting from each column vector $X_i^k$ of $X^k$ the vector $\overline{M}_k$ is referred to herein as the "centralized matrix", and is denoted by "$X^k - \overline{M}_k$".

The covariance of $$X^k \text{ is } C_k = 1/M_k * \sum_{i=1}^{m} (X_i^k - M_k)^t (X_i^k - M_k).$$

The mean vector $\overline{M}_k$ is of dimension $N \times 1$ while the covariance $C_k$ is of dimension $M_k \times M_k$.

Given a tissue sample to be classified, the expression level of the N genes in the tissue sample is obtained for each of the genes $j=1, \ldots N$, to produce an N-dimensional vector $\tilde{X} = (\tilde{x}_1 \ldots \tilde{x}_N)$.

For each of the classes k, k=1 to K, a metric $\mu_k$ is calculated indicative of the distance or extent of dissimilarity between the vector $\tilde{X}$ and the database $X^k$ of data relating to the class k. In accordance with the invention, the metric $\mu_k$ is obtained using an algebraic expression involving one or more of the eigenvectors of $C_k$. The tissue sample is then classified in the class $\tilde{k}$, where $\tilde{k}$ is the value of k for which $\mu_k$ is minimal.

In a preferred embodiment of the invention, the eigenvalues and eigenvectors of $C_k$ are calculated and a transformation matrix $A_k$ is constructed whose rows are the eigenvectors of $C_k$ arranged in a decreasing order constructed to their corresponding eigenvalues:

$$A_k = \begin{vmatrix} e_{11}^k & e_{12}^k & & e_{1M_k}^k \\ e_{21}^k & e_{22}^k & & e_{2M_k}^k \\ \vdots & \vdots & & \vdots \\ e_{M1}^k & e_{M2}^k & & e_{M_k M_k}^k \end{vmatrix}$$

The centralized matrix $\tilde{X} - \overline{M}_k$, is multiplied by the matrix A (a transform known as the "Hotelling transform") to produce the matrix $Y_k$, where $Y_k = (X - \overline{M}_k)A$. The metric $\mu_k$ is given by $\mu_k = (\tilde{X} - \overline{M}_k) - Y_k Y_k^t (\tilde{X} - \overline{M}_k)$. In this metric, $Y_k Y_k^t (\tilde{X} - \overline{M}_k)$ is a reconstruction of $\tilde{X} - \overline{M}_k$ based upon the eigenvectors of $C_k$, and the metric $\mu_k$ measures the difference between $\tilde{X} - \overline{M}_k$ and its reconstruction.

In a preferred embodiment, the database $X^k$ is constructed so that the set of column vectors $X_i^k$ describes as large a domain as possible. This may be achieved by searching and selecting the least correlated set from the available $X_i^k$. For example, the available $X_i^k$ may be split into clusters using k-means, and from each cluster selecting an $X_i^k$ with the minimum distance to the cluster's center.

Thus, in its first aspect, the invention provides a method for classifying a test tissue sample into a class from among K classes, comprising:
(a) providing a gene expression vector $\tilde{X} = (\tilde{x}_1, \ldots \tilde{x}_N)$ of the test tissue sample where $\tilde{x}_j$ is an expression level of a gene j in the test tissue sample;
(b) for k=1 to K
  (i) for each of $M_k$ tissue samples in the class k,
    (I) for each of the N genes, providing a gene expression matrix $X^k = (X_{ij}^k)$, where $X_{ij}^k$ is an expression level of the jth gene in the ith tissue sample, where j=1 to N and i=1 to $M_k$;
  (ii) calculating a centralized matrix $X^k - \overline{M}_k$, where $$\overline{M}_k = 1/M_k * \sum_{i=1}^{M} X_i^k, \text{ and } X_i^k = \begin{pmatrix} x_{i1}^k \\ x_{i2}^k \\ \vdots \\ x_{iN}^k \end{pmatrix};$$

(iii) calculating a covariance matrix $C_k$ of $X^k - \overline{M}_k$;
  (iv) calculating one or more eigenvectors of the matrix $C_k$;
  (v) calculating a metric $\mu_k$ indicative of an extent of dissimilarity between the vector $\tilde{X}$ and the matrix $X^k$, the metric k being calculated using an algebraic expression involving one or more eigenvectors of the matrix $C_x$, and
(c) classifying the test tissue sample into a class $\tilde{k}$, where $\tilde{k}$ is a class for which the metric $\mu_k$ is minimum among the k classes.

In its second aspect, the invention provides a program storage device readable by machine, tangibly embodying a program of instructions executable by the machine to perform method steps for classifying a test tissue sample into a class from among K classes, the test tissue sample having a gene expression vector $\tilde{X} = (\tilde{x}_1, \ldots \tilde{x}_N)$ where $\tilde{x}_j$ is an expression level of a gene j in the test tissue sample, comprising:
(a) for k=1 to K
  (i) for each of $M_k$ tissue samples in the class k,
    (I) for each of the N genes, calculating a centralized matrix $X^k - \overline{M}_k$, where $X^k = (X_{ij}^k)$, a gene expression matrix in which $X_{ij}^k$ is an expression level of the jth gene in the ith tissue sample, where j=1 to N and i=1 to $M_k$; and where $$\overline{M}_k = 1/M_k * \sum_{i=1}^{M} X_i^k, \text{ and } X_i^k = \begin{pmatrix} x_{i1}^k \\ x_{i2}^k \\ \vdots \\ x_{iN}^k \end{pmatrix};$$

(ii) calculating a covariance matrix $C_k$ of $X^k - \overline{M}_k$;
  (iii) calculating one or more eigenvectors of the matrix $C_k$;
  (iv) calculating a metric $\mu_k$ indicative of an extent of dissimilarity between the vector $\tilde{X}$ and the matrix $X^k$, the metric $\mu_k$ being calculated using an algebraic expression involving one or more eigenvectors of the matrix $C_x$, and
(b) classifying the test tissue sample into a class $\tilde{k}$, where $\tilde{k}$ is a class for which the metric $\mu_k$ is minimum among the k classes.

In its third aspect, the invention provides a computer program product comprising a computer useable medium having computer readable program code embodied therein for classifying a test tissue sample into a class from among K classes, the computer program product comprising:

(a) Computer readable program code for causing the computer, for k=1 to K
  (i) for each of $M_k$ tissue samples in the class k,
    (I) for each of the N genes, to calculate a centralized matrix $X^k - \overline{M}_k$, where $X^k = (X_{ij}^k)$, a gene expression matrix in which $X_{ij}^k$ is an expression level of the jth gene in the ith tissue sample, where j=1 to N and i=1 to $M_k$; and where $$\overline{M}_k = 1/M_k * \sum_{i=1}^{M} X_i^k, \text{ and } X_i^k = \begin{pmatrix} x_{i1}^k \\ x_{i2}^k \\ \vdots \\ x_{iN}^k \end{pmatrix};$$

(ii) computer readable program code for causing the computer to calculate a covariance matrix $C_k$ of $X^k - \overline{M}_k$;
  (iii) computer readable program code for causing the computer to calculate one or more eigenvectors of the matrix $C_k$;
  (iv) computer readable program code for causing the computer to calculate a metric $\mu_k$ indicative of an extent of dissimilarity between the vector $\tilde{X}$ and the matrix $X^k$, the metric $\mu_k$ being calculated using an algebraic expression involving one or more eigenvectors of the matrix $C_x$, and
(b) computer readable program code for causing the computer to classify the test tissue sample into a class $\tilde{k}$, where $\tilde{k}$ is a class for which the metric $\mu_k$ is minimum among the k classes.

In its fourth aspect, the invention provides a computer program comprising computer program code means for performing all the steps of the method of the invention when said program is run on a computer.

In its fifth aspect, the invention provides a computer program of the invention embodied on a computer readable medium.

In its sixth aspect, the invention provides a kit comprising
(a) means for obtaining a gene expression vector $\tilde{X} = (\tilde{x}_1, \ldots \tilde{x}_N)$ for one or more tissue samples where $\tilde{x}_j$ is an expression level of a gene j in the tissue sample;
(b) a computer readable medium embodying a computer program comprising computer program code means for performing all the steps of the method of the invention when said program is run on a computer; and
(c) instructions for carrying out the method.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

EXAMPLES

The invention was tested on tumor gene expression data available from the multiclass cancer diagnosis set of Ramaswamy et al. (2001). As disclosed in that publication, sixteen different cancer classes were defined (K=16). For each class k, a level of gene expression for each of 16,063 genes was obtained for each of 10 tissue samples known to belong to the class (N=16,063). The databases $X^k$ were obtained using two microarrays made by Affymetrix—the M6800 and the SK35. Of the 16 different cancer types, 2 included sub-type data: leukemia consisting of 3 groups—AML, ALL B-type, ALL T-type and lymphoma consisting of 2 groups, (Lymph Folli and Lymph Large_B).

For each class k, 9 microarrays were selected from among the 10 for use in the database $X^k$ (Mk=9). 9 out of the 10 microarrays were used in each set, and when a tested microarray to be classified $\tilde{X}$ was included among the 9, it was replaced with the tenth microarray. For each class k, the metric $\mu_k = (\tilde{X} - \overline{M}_k) - Y_k Y_k^t (\tilde{X} - \overline{M}_k)$, as defined above, was used. For each tested microarray, the metric $\mu_k$ was plotted as a function of k. A tested microarray was classified in the class $\tilde{k}$ where $\tilde{k}$ is the value of k for which $\mu_k$ is minimum.

Results

Figure 1:
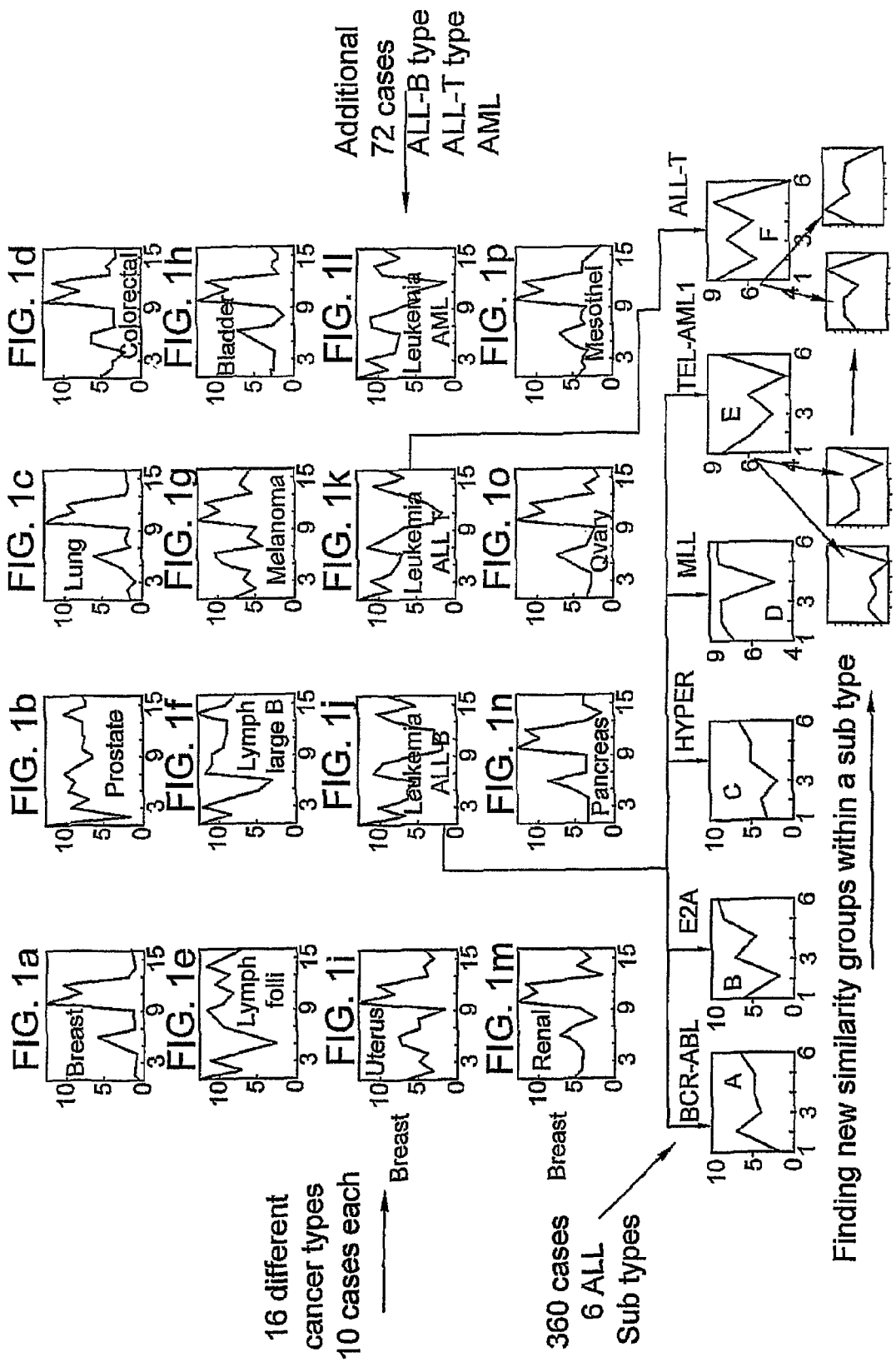
FIG. 1 shows, for each of 16 tissue samples, the graph of the metric $\mu_k$ for each of 16 classes in accordance with one embodiment of the invention, where the tissue samples are (a) breast cancer, (b) prostate cancer, (c) lung cancer, (d) colorectal cancer, (e) lymph_follicular cancer, (f) lymph_large_B cancer, (g) melanoma, (h) urinary bladder cancer, (i) uterine cancer, (j) leukemia_ALL_B, (k) leukemia_ALL_T, (l) leukemia_ALL_AML, (m) renal cancer, (n) pancreatic cancer, (o) ovarian cancer and (p) mesothelial cancer, and the 16 categories are (1) breast cancer, (2) prostate cancer, (3) lung cancer, (4) colorectal cancer, (5) lymph_Follicular cancer, (6) lymph_large_B cancer, (7) melanoma, (8) urinary bladder cancer, (9) uterine cancer, (10) leukemia_ALL_B, (11) leukemia_ALL_T, (12) leukemia_ALL_AML, (13) renal cancer, (14) pancreatic cancer, (15) ovarian cancer and (16) mesothelial cancer.

The graphs of $\mu_k$ as a function of k, for each of the 16 different tissue samples that were tested are shown in FIG. 1.

In one experiment, the entire gene set was used, (excluding the control probes on the microarrays). Column a of Table 1 shows the number of accurate classifications that were made out of the 9 classifications that were made in each of the 16 categories. The number of genes in each class having an expression level above 500 and 50000 is indicated in columns c and d of Table 1. The accuracy of the classification was in direct correlation with the number of active genes in each group. For example, in Prostate cancer tissues there are 4000 active genes having an expression level greater than 5000 and the accuracy achieved was 2 out of 9 cases, whereas in the ALL-T type class, there are 28000 such active genes and an accuracy was achieved of 9 out of 9.

In order to compensate for the effect of the variability in the number of active genes among the different classes, low level "noisy genes" were filtered out by replacing the ith row of $X^k$ with 0 when $X_{ij}^k$ was below a threshold value of 100 for at least one value of j. Column b of Table 1 shows the improvement resulting from zeroing out all genes having an expression level less than 100. In 10 cancer classes, 9 out of the 9 test cases where correctly classified and in the other 6 cancer classes 8 out of the 9 test cases where correctly classified. Overall 138 out of 144 cases were correctly classified, an accuracy of 96%. In comparison, Ramaswamy et al. (2001) using SVM supervised classifier with OVA (one versus all) approach, reached an accuracy of 78% with this data-set.

TABLE 1

Number of successful classifications from 9 cases per each cancer category (Columns a and b), and the number of genes above a threshold level of 5000 and 500 in each category (columns c and d).

| Type of test | (a) All control probes | (b) Filtered genes zeroed | (c) Number of genes >5000 | (d) Number of genes >500 |
|---|---|---|---|---|
| Breast | 2 | 8 | 160 | 4008 |
| Prostate | 6 | 8 | 1267 | 24831 |
| Lung | 3 | 8 | 483 | 10486 |
| Colorectal | 5 | 9 | 853 | 12789 |
| Lymph_Folli | 8 | 9 | 905 | 18610 |
| Lymph_Large_B | 6 | 9 | 1406 | 26329 |
| Melanoma | 5 | 8 | 557 | 9143 |
| Bladder | 7 | 8 | 267 | 6146 |
| Uterus | 7 | 9 | 1008 | 13110 |
| Leukemia_ALL_B | 8 | 9 | 2189 | 34674 |
| Leukemia_ALL_T | 9 | 9 | 2773 | 28931 |
| Leukemia_ALL_AML | 7 | 8 | 2548 | 34700 |
| Renal | 6 | 8 | 755 | 16865 |
| Pancreas | 6 | 9 | 625 | 9458 |
| Ovary | 4 | 9 | 727 | 13516 |
| Mesothel | 8 | 9 | 834 | 14952 |

To test the method of the invention on data sets where all clinical cancer classes have a similar number of genes that are well expressed, a second test was performed on genes expressed in leukemic blasts from 360 pediatric ALL patients samples. Gene expression levels were obtained from Eng-Juh Yeoh et al. (2002). The distinct expression profiles identified each of the prognostically important leukemia subtypes, including T-ALL, E2A-PBX1, BCR-ABL, TEL-AML1, MLL rearrangement, and hyperdiploid>50 chromosomes. 10 cases were randomly selected for creating the databases $X^k$.

Figure 2:
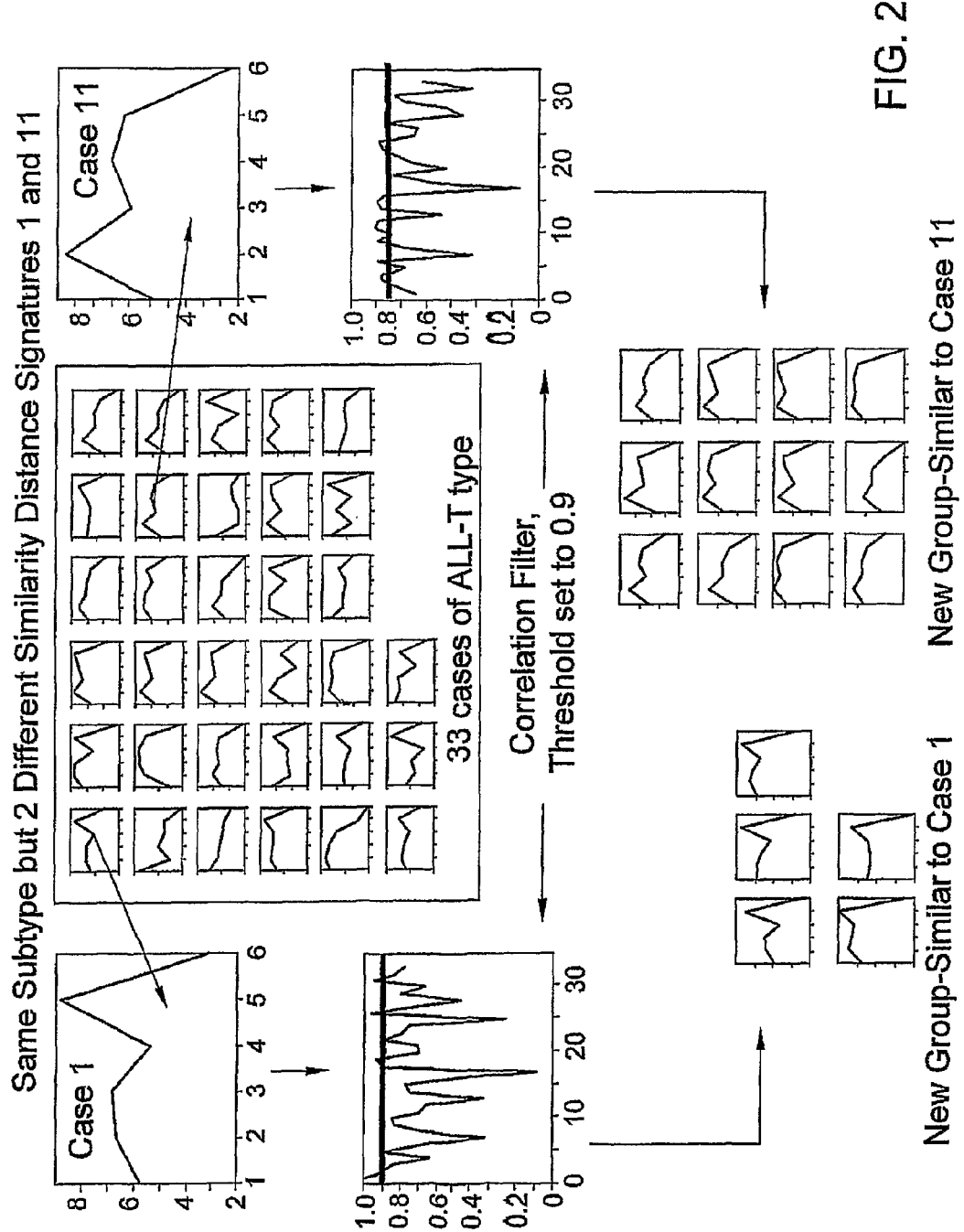
FIG. 2 shows the identification of patients with 2 different prototype profiles. Correlation values range from 0 to 1, where 1 is an identical signature. Values greater than 0.9 were selected.

The invention also allows the identification of new sub-classes in an existing class by dividing tissue samples classified into a particular class by the method of the invention into sub-classes, where the metric $\mu_k$ of any two tissue samples in a given sub-class have an auto correlation above a predetermined threshold. As shown in FIG. 2, the metric $\mu_k$ of each class was plotted as a function of k. By measuring the correlation between pairs of $\mu_k$ for any pair of tissues in the class, previously unknown sub-classes were identified.

To examine the method on a larger dataset where it is possible to use a separate part of the data for forming the databases $X^k$ and another part as a test set, the dataset of 12,600 genes expressed in leukemic blasts from 360 pediatric ALL patients was used. The ALL was broken into 6 groups—T-ALL, E2A-PBX1, BCR-ABL, TEL-AML1, MLL rearrangement, and hyperdiploid>50 chromosomes. In the first examination of the method the first 10 microarrays were selected from each of the 6 subtypes to construct $X^k$. The results are shown in Table 2, row 1 An accuracy of 76.6% (144 out of 188 correctly classified). The accuracy was increased by improving the selection of the 10 representing cases, so that they describe a larger domain of their subtype. This was achieved by searching and selecting the least correlated set from the available cases. For example, the data in each set was split into 10 clusters using k-means, and from each cluster was selected the case with the minimum distance to the cluster's center. As shown in Table 2, row 2, an accuracy of 91.5% (172 out of 188 correctly classified) was achieved. The accuracy was also improved by increasing the number of microarrays used use for constructing $X^k$ ($M_k$). Three out of the six subtypes were large enough to allow increasing $M_k$ from 10 to 25 cases. As shown in Table 2, row 3, an accuracy of 98.2% (109 out of 111 correctly classified) was achieved.

TABLE 2

Number of Correct classifications in 6 ALL sub-types: T-ALL, E2A-PBX1, Hyperdiploid >50, MLL rearrangement, TEL-AML1, T-ALL

| | Correct classification | | | | | | Overall Accuracy |
|---|---|---|---|---|---|---|---|
| | ber | E2a | hyper | mll | tel | t-all | |
| Using the first 10 cases as a coordinate base. | 4/5 | 15/1 | 39/54 | 9/10 | 46/69 | 31/33 | 144/188 76/6% |
| Using selected 10 uncorrelated cases | 4/5 | 15/17 | 48/54 | 9/10 | 65/69 | 31/33 | 172/188 91.5% |
| Using 25 cases as a coordinate base | | | 37/39 | | 54/54 | 18/18 | 109/111 98/2% |

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

References:

Ramaswamy, Tamayo, Rifkin, Mukherjee, Yeang, Angelo, Ladd, Reich, Latulippe, Mesirov, Poggio, Gerald, Loda, Lander, Golub. (2001) "Multiclass cancer diagnosis using tumor gene expression signatures" Proc. Natl. Acad. Sci. U.S.A., 98,15149.

Enj-Juh, Y., E., Ross, E., Downing, R. et al. (2002) "Classification, subtype discovery, and prediction of outcome in pediatric acute lymphoblastic leukemia by gene expression profile." Cancer Cell, 1,133-143.

The invention claimed is:

1. A method for classifying a test tissue sample into a class from among K classes, comprising:
   (a) providing a gene expression vector $\tilde{X}=(\tilde{x}_1, \ldots \tilde{x}_N)$ of the test tissue sample where $\tilde{x}_j$ is an expression level of a gene j in the test tissue sample;
   (b) for k=1 to K
   using a processor to perform the following steps:
      (i) for each of $M_k$ tissue samples in the class k,
         (I) for each of the N genes, providing a gene expression matrix $X^k=(X_{ij}^k)$, where $X_{ij}^k$ is an expression level of the jth gene in the ith tissue sample, where j=1 to N and i=1 to $M_k$;
      (ii) calculating a centralized matrix $X^k - \overline{M}_k$, where $$\overline{M}_k = 1/M_k * \sum_{i=1}^{M} X_i^k, \text{ and } X_i^k = \begin{pmatrix} x_{i1}^k \\ x_{i2}^k \\ \vdots \\ x_{iN}^k \end{pmatrix};$$

(iii) calculating a covariance matrix $C_k$ of $X^k - \overline{M}_k$;
      (iv) calculating one or more eigenvectors of the matrix $C_k$;
      (v) calculating a metric $\mu_k$ indicative of an extent of dissimilarity between the vector $\tilde{X}$ and the matrix $X^k$, the metric k being calculated using an algebraic expression involving one or more eigenvectors of the matrix $C_x$, and (c) classifying the test tissue sample into a class $\tilde{k}$, where $\tilde{k}$ is a class for which the metric $\mu_k$ is minimum among the k classes.

2. The method according to claim 1 wherein calculating a metric $\mu_k$ comprises:
   (a) calculating a transformation matrix $A_k$ whose rows are the eigenvectors of $C_k$ arranged in a decreasing order according to their corresponding eigenvalues;
   (b) calculating $Y_k$, where $Y_k = (X - \overline{M}_k) A$; and
   (c) calculating $\mu_k$ using the algebraic expression $\mu_k = (\tilde{X} - \overline{M}_k) - Y_k Y_k^T (\tilde{X} - \overline{M}_k)$.

3. The method according to claim 1, wherein a gene expression level is determined at the level of transcription, translation or protein processing.

4. The method according to claim 1, wherein one or more gene expression levels is obtained using a microarray analysis, Southern blotting, or Western blotting.

5. The method according to claim 1, wherein at least one of the classes is a diseased state of the tissue.

6. The method according to claim 5, wherein one or more of the diseases states is cancer.

7. The method according to claim 6 wherein one or more of the disease states is a cancer selected from breast cancer, prostate cancer, lung cancer, colorectal cancer, lymph-Follicular cancer, lymph-large-B cancer, Melanoma, urinary bladder cancer, Uterine cancer, Leukemia-ALL-B, Leukemia-ALL-T, Leukemia-ALL-AML, renal cancer, pancreatic cancer, ovarian cancer and mesothelial cancer.

8. The method according to claim 1, wherein at least one of the classes is a response to a treatment.

9. The method according to claim 8, wherein the treatment is a drug treatment or chemotherapy.

10. The method according to claim 1, wherein at least one of the classes is a state selected from a state of remission and a state of relapse.

11. The method according to claim 1, further comprising replacing the values of $X_{ij}^k$ in one or more rows of one or more of the $X^k$ with zero if one or more of the $X_{ij}^k$ in the row is below a predetermined level.

12. The method according to claim 1, wherein the one or more of the gene expression matrices $X^k$ is constructed by searching and selecting a least correlated sub-set from a set of available $X_i^k$.

13. The method according to claim 12 wherein one or more of the gene expression matrices $X^k$ is constructed by splitting the set of available $X_i^k$ into clusters using k-means, and from each cluster selecting an $X_i^k$ having a minimum distance to the cluster's center.

14. A program storage device readable by machine, tangibly embodying a program of instructions executable by the machine to perform method steps for classifying a test tissue sample into a class from among K classes, the test tissue sample having a gene expression vector $\tilde{X} = (\tilde{x}_1, \ldots \tilde{x}_N)$ where $\tilde{x}_j$ is an expression level of a gene j in the test tissue sample, comprising:
   a computer-readable medium comprising:
   (a) for k=1 to K
      (i) for each of $M_k$ tissue samples in the class k,
         (I) for each of the N genes, calculating a centralized matrix $X^k - \overline{M}_k$, where $X^k = (X_{ij}^k)$, a gene expression matrix in which $X_{ij}^k$ is an expression level of the jth gene in the ith tissue sample, where j=1 to N and i=1 to $M_k$; and where $$\overline{M}_k = 1/M_k * \sum_{i=1}^{M} X_i^k, \text{ and } X_i^k = \begin{pmatrix} x_{i1}^k \\ x_{i2}^k \\ \vdots \\ x_{iN}^k \end{pmatrix};$$

(ii) a first instruction for calculating a covariance matrix $C_k$ of $X^k - \overline{M}_k$;
   (iii) a second instruction for calculating one or more eigenvectors of the matrix $C_k$;
   (iv) a third instruction for calculating a metric $\mu_k$ indicative of an extent of dissimilarity between the vector $\tilde{X}$ and the matrix $X^k$, the metric $\mu_k$ being calculated using an algebraic expression involving one or more eigenvectors of the matrix $C_x$, and
   (b) classifying the test tissue sample into a class $\tilde{k}$, where $\tilde{k}$ is a class for which the metric $\mu_k$ is minimum among the k classes.

15. A computer program product comprising a computer readable medium comprising computer readable program code embodied therein for classifying a test tissue sample into a class from among K classes, the computer program product comprising:
   (a) computer readable program code, for k=1 to K
      (i) for each of $M_k$ tissue samples in the class k,
         (I) for each of the N genes, to calculate a centralized matrix $X^k - \overline{M}_k$, where $X^k = (X_{ij}^k)$, a gene expression matrix in which $X_{ij}^k$ is an expression level of the jth gene in the ith tissue sample, where j=1 to N and i=1 to $M_k$; and where $$\overline{M}_k = 1/M_k * \sum_{i=1}^{M} X_i^k, \text{ and } X_i^k = \begin{pmatrix} x_{i1}^k \\ x_{i2}^k \\ \vdots \\ x_{iN}^k \end{pmatrix};$$

(ii) a first instruction to calculate a covariance matrix $C_k$ of $X^k - \overline{M}_k$;
   (iii) a second instruction to calculate one or more eigenvectors of the matrix $C_k$;
   (iv) a third instruction to calculate a metric $\mu_k$ indicative of an extent of dissimilarity between the vector $\tilde{X}$ and the matrix $X^k$, the metric $\mu_k$ being calculated using an algebraic expression involving one or more eigenvectors of the matrix $C_x$, and
   (b) a further instruction to classify the test tissue sample into a class $\tilde{k}$, where $\tilde{k}$ is a class for which the metric $\mu_k$ is minimum among the k classes.

* * * * *